United States Patent [19]

Skogerson

[11] 4,348,483

[45] Sep. 7, 1982

[54] METHOD FOR THE PRODUCTION OF CHROMIUM YEAST

[75] Inventor: Lawrence E. Skogerson, Milwaukee, Wis.

[73] Assignee: Universal Foods Corporation, Milwaukee, Wis.

[21] Appl. No.: 227,962

[22] Filed: Jan. 23, 1981

[51] Int. Cl.$^3$ .......................... C12N 1/16; C12N 1/18
[52] U.S. Cl. .................................... 435/255; 435/256; 424/195
[58] Field of Search ................................ 435/255, 256

[56] References Cited

PUBLICATIONS

Mertz, Chromium Occurence and Function in Biological Systems, Physiological Reviews, vol. 49, No. 2, (1969), pp. 189–192.

Anderson et al., An Improved Assay for Biologically Active Chromium, Journal of Agricultural Food Chemistry, vol. 26, No. 5, (1978), pp. 1219–1221.

*Primary Examiner*—Joseph M. Golian
*Attorney, Agent, or Firm*—Neuman, Williams, Anderson & Olson

[57] ABSTRACT

A method of producing a chromium yeast product having a high intracellular chromium content which is useful as a dietary chromium supplement is provided by treating an aqueous suspension of live yeast cells adjusted to an acidic pH in the range of 4 to about 7 with a water-soluble non-toxic chromium salt under essentially non-growth conditions for a period sufficient to permit the absorption of a significant amount of intracellular chromium ion by said yeast cells. The yeast cells so treated may be concentrated, washed free of extracellular chromium salts and dried or further grown by the addition of nutrients to the media, said growth period being of sufficient duration to reduce the intracellular chromium content of the yeast to a predetermined level followed by recovery, washing and drying of the chromium yeast as aforesaid.

14 Claims, No Drawings

METHOD FOR THE PRODUCTION OF CHROMIUM YEAST

FIELD OF THE INVENTION

This invention relates to a method for the preparation of yeast containing substantial amounts of intracellular chromium, useful as a supplemental dietary source of metabolizable chromium where additional chromium is indicated.

DESCRIPTION OF THE PRIOR ART

While the role of chromium in mammalian diets is not completely understood, substantial evidence has accumulated associating dietary chromium deficiency with decreased ability of peripheral tissues to take up glucose from the blood. This condition is symptomatically similar to diabetes but is distinguished from it by the presence of normal insulin levels. There is also evidence that normal biological activity of insulin is dependent on a sufficient level of chromium. Since chromium is lost daily through excretion, a diet deficient in assimilable chromium will lead to glucose intolerance. Thus, some studies such as that of Mertz, Physiological Review, Vol. 49 No. 2 (1969) pp. 189-192 have shown that diets low in chromium, led to a progressive impairment of intravenous glucose tolerance in rats when fed over a period of several weeks. The observed impairment of glucose tolerance was eliminated by supplementing the basal diet wth a small percentage of brewer's yeast which supplied an unknown principal designated as the "Glucose Tolerance Factor" (GTF). The studies conducted suggested that the observed improved GTF activity was attributable to an organic trivalent chromium complex present in the brewer's yeast additive. Additional experiments indicated that the form of the chromium in the brewer's yeast was readily metabolizable but that attempts to supplement a diet by the addition of inorganic chromium salts did not achieve a comparably efficient effect. More particularly, inorganic chromium salts added to the diet or even naturally occurring chromium present in certain diets such as commercial animal chows, was not effective to prevent impairment of the glucose tolerance function indicating that the chromium in the diet was in non-utilizable form.

Similar confirmatory work was later reported by Anderson, et al. in the *Journal of Agricultural Food Chemistry*, Vol. 26 No. 5 (1978) pp. 1219-21. In that paper it was observed that chromium metabolism differs from that of other trace elements in its strict dependence on the chemical form in which the element is present. Specifically, it was noted that natural organic chromium complexes isolated from brewer's yeast or certain other natural products differed from simple inorganic chromium compounds in respect to the rate of intestinal absorption, tissue distribution, and in other effects. When chromium deficiency occurs, dietary supplementation with high levels of inorganic chromium compounds is needed to restore chromium sufficiency, as contrasted to the much lower levels of organically bound chromium that are required to counteract nutritional deficiency. The conclusion was reached that total dietary chromium is not a meaningful indicator of the chromium nutriture of animals.

Although it is known that brewer's yeast (*Saccharomyces uvarum*) contains small amounts of organically bound chromium in a utilizable form, the concentration is usually quite low (2 to 4 $\mu g/g$ yeast solids). Moreover, the use of large amounts of brewer's yeast in a diet is not necessarily feasible in view of the low and variable concentration of chromium. Other forms of commercial yeast such as bakers' yeast, *Saccharomyces cerevisiae* and Torula are characterized by the essential absence of chromium.

Since the organically bound form of chromium found in brewer's yeast is known to be both assimilable and efficient as a dietary source of chromium to alleviate deficiencies and impaired glucose tolerance, it would be desirable to provide supplemental chromium in a more concentrated usable form that could be used in small amounts as a dietary chromium supplement.

Initial attempts to grow a yeast such as bakers' yeast in a media which was enriched by the addition of inorganic chromium salts did not achieve the desired increase in organically bound intracellular chromium. Moreover, it was observed that increasing the chromium salt concentration in the media did not increase the intracellular content of organically bound chromium.

OBJECTS OF THE INVENTION

Accordingly, one of the objects of the present invention is the provision of a method for producing a chromium yeast having an enhanced intracellular chromium content.

Another object is the provision of a method for producing a yeast having high levels of organically bound chromium in an assimilable form.

A further object is the provision of a method and process for producing an edible yeast food product having a high intracellular chromium content which is useful as a dietary supplement for chromium deficient conditions.

A still further object is the provision of a food product having a high concentration of assimilable chromium which food product is useful as a dietary supplement to alleviate glucose intolerance due to chromium deficiency.

A final object is the provision of a yeast food having an essentially uniformly distributed intracellular chromium content.

SUMMARY OF THE INVENTION

The foregoing objects are achieved by a process for preparing a chromium yeast product which has a high intracellular, organically bound, assimilable chromium content, which process comprises contacting live yeast cells in an aqueous suspension under controlled acidic pH conditions above pH 4 with predetermined, non-inhibitory amounts of a non-toxic, water-soluble chromium salt in a non-growth pretreating phase to permit substantial and significant intracellular absorption of chromium by said yeast cells in an amount greater than a predetermined final amount in said yeast, thereafter adding nutrients to induce a growth phase of said yeast cells and reduce the intracellular chromium content of said yeast cells to the said final predetermined level and, recovering, concentrating and washing said yeast cells free of extracellular chromium salts; pasteurizing, and drying said yeast cells to produce a dry yeast pulverulent product.

More particularly, the present invention in another broad form includes a process for producing a chromium yeast which comprises:

(a) adjusting the pH of an aqueous suspension of live yeast cells to from about 4 to about 7;

(b) treating the aqueous suspension of live yeast cells with a water-soluble, non-toxic chromium salt at a chromium ion concentration based on yeast cell solids that is below the concentration at which an inhibitory effect on the growth of the yeast is observed;

(c) maintaining the suspension for an essentially non-growth pre-treatment period sufficient to permit substantial intracellular absorption of chromium by said yeast cells;

(d) adding yeast growth nutrients to the aqueous medium containing the chromium treated yeast and inducing growth of the said yeast to thereby dilute the intracellular chromium content of said yeast to a predetermined level;

(e) recovering and concentrating the yeast cells from the aqueous growth medium;

(f) washing the recovered yeast cells to remove extracellular chromium salts; and (g) pasteurizing and drying the washed yeast cells containing a substantial amount of intracellular chromium ion.

In another broad form the present invention also relates to a method of preparing a chromium yeast product which has a high intracellular chromium content which comprises adjusting the pH of an aqueous suspension of live yeast cells to from about 4 to about 7, treating the aqueous suspension of live yeast cells with a water-soluble, non-toxic chromium salt at a chromium ion concentration of from about 200 to about 8000 $\mu g/g$ of yeast cell solids, maintaining said yeast cells in contact with chromium ion at said pH levels under essentially non-growth conditions for a period of at least about 5 to 30 minutes until said yeast cells have intracellularly absorbed a substantial amount of chromium ion, recovering and concentrating the yeast cells from the aqueous medium; washing the recovered yeast cells to remove extracellular chromium salts; pasteurizing, and drying the washed yeast cells containing a substantial amount of intracellular chromium.

The yeast employed in the process of the present invention is preferably a food grade or edible yeast and most preferably *Saccharomyces cerevisiae*. Other yeasts which can be used include Torula and brewer's yeast such as *Saccharomyces carlsbergensis* or, by its preferred name, *S. uvarum*.

The chromium salts used to treat the seed yeast are water-soluble, non-toxic chromium salts of which chromic chloride hexahydrate ($CrCl_3 \cdot 6H_2O$) is preferred, although other chromium salts such as the bromide, acetate, nitrate salts or the like may also be used. The amount of chromium salt used should be sufficient to provide a chromium ion concentration of from about 200 to 8000 $\mu g/g$ of yeast solids preferably from about 500 to about 6000 and most preferably from about 1000 to 4000 $\mu g/g$ of yeast solids in the uptake or pre-treatment phase.

The absorption of chromium by the yeast in the pre-treatment or uptake step or period has been determined to be influenced by the factors of time, chromium ion and yeast cell concentrations and pH. The pre-treatment or uptake period is an essentially non-growth period where the yeast cells are in an aqueous suspension in the presence of the dissolved chromium salt. The pre-treatment or uptake time period is at least about 5 minutes, or preferably from about 5 to 30 minutes. It has been determined that pre-treatment times of greater than 30 minutes do not substantially increase the absorption levels of intracellular chromium by the yeast cells, so that extended pre-treatment times are not economic.

It has also been determined that addition of soluble chromium salts to the seed yeast during the growth phase or the fermentation of the yeast does not result in any significant absorption of the chromium by the yeast cells.

The pH of the pre-treatment or uptake medium is essentially in the acid range particularly of from about 4 to about 7, or preferably from 4 to 6. It has been observed that at the lower pH's (about 4 to 4.5) the amount of absorption is relatively low even after a pre-treatment time of about 30 minutes. Generally, the most preferred pH range is from about 5 to about 6.

Below about pH 4.0, very little uptake occurs. As the pH is increased from about 4 to 4.5 to about 6, the fraction of chromium ion taken up by a given amount of yeast increases. If the concentration of intracellular chromium in the seed yeast exceeds about 1000 $\mu g/g$, subsequent growth is severely restricted. Thus, the pre-treatment pH, the chromium salt concentration, and the yeast concentration must be adjusted so that the resulting level of chromium absorbed in the seed yeast is less than about 1000 $\mu g/g$.

After the seed yeast cells are subjected to the chromium treatment and absorption of chromium ion by the yeast is essentially maximized or equilibrated, the growth phase of the yeast is initiated by the addition of nutrients to the yeast. A desideratum is to achieve an intracellular chromium absorption by the seed yeast to a level higher than that ultimately desired in the final yeast product. Then the yeast is grown to reduce the absorbed chromium to the level desired. It is believed that this assures that the chromium is in the organically bound assimilable form desired.

The growth phase is usually carried out at a pH of from 4.8 to 5.5, preferably at about 5. The temperature is preferably between about 25° and 35° C., with about 29°–30° C. being preferred.

The nutrients include a source of carbohydrate or carbon such as molasses. Other nutrient salts are exemplified by potassium chloride (KCl), magnesium sulfate ($MgSO_4 \cdot 7H_2O$), and nitrogen and phosphorous sources such as ammonium dihydrogen phosphate [$(NH_4)H_2PO_4$], ammonia, and phosphoric acid.

The pH during the growth period is adjusted to about 5 after the uptake treatment is complete. The growth of the yeast is continued for sufficient time until the intracellular chromium content of the yeast reaches a predetermined level. Usually, the yeast cell multiplications are from at least one (100% increase) to about a seven-fold increase, preferably a four-fold increase. The fermentation or yeast growth is usually carried out over a period of at least up to from about 4 to about 17 hours to achieve these increases.

After the yeast cells have multiplied in the growth phase to produce yeast cells with the desired predetermined intracellular chromium level (e.g. 40–200 $\mu g/g$ of yeast solids as a preferred example), the yeast is recovered from the fermentor, concentrated by centrifugation or other equivalent means and washed with water to remove extracellular inorganic chromium salts as well as other solubles.

The resulting yeast cream of washed yeast cells having a substantial intracellular chromium content is then pasteurized and drum dried to kill the yeast. The resulting yeast powder is then ready for packaging (or tableting) and sale to the consumer as a yeast food that may be used as a dietary supplement of organically bound, assimilable chromium.

DESCRIPTION OF THE PREFERRED EMBODIMENTS

A series of experiments were conducted to determine the effect of pH on uptake of chromium ion by the seed yeast during a pre-treatment period of 30 minutes.

EXAMPLE I

In these experiments, the aqueous suspension of seed yeast at 1% solids level was treated with chromic chloride ($CrCl_3 \cdot 6H_2O$) at levels of 190 mg/l at various pH levels. The results are shown in Table I following. The percentage uptake shown is the amount of analyzed intracellular chromium absorbed by the yeast as compared to the initial concentration in the pre-treatment step.

TABLE I
The Effect of pH on Uptake of $Cr^{+3}$ by Yeast

| Treatment pH | Intracellular $Cr^{+3}$ in Yeast Product (μg/g yeast solids) | % Uptake |
|---|---|---|
| 4.0 | 153 | 4.6 |
| 4.5 | 216 | 6.5 |
| 5.0 | 413 | 12.4 |
| 5.25 | 527 | 15.8 |
| 5.5 | 633 | 19.0 |
| 6.0 | 976 | 29.3 |

From the foregoing, it is evident that low pH's are inefficient in the promotion of chromium absorption by the seed yeast. The best results are obtained at pH 5 and above.

EXAMPLE 2

A second series of pre-treatment experiments were conducted to demonstrate the effect of initial concentration of chromium ion on the final chromium intracellular content of the yeast cells. The conditions were the same as in Example I except that the amount of chromium used in the pre-treatment was varied as shown in Table II and the pre-treatment pH was 5.25. The results are shown in Table II:

TABLE II

| $CrCl_3 \cdot 6H_2O$ Added (mg/liter) | Intracellular $Cr^{+3}$ in Yeast Product (μg/g yeast solids) |
|---|---|
| 95 | 350 |
| 190 | 527 |
| 285 | 740 |

While the foregoing shows that the uptake of chromium by the seed yeast during the pre-treatment period is proportional to the concentration of chromium, the benefits are decreasing with the increasing concentration.

The following examples illustrate the process of the present invention in experiments in which the pre-treatment period was followed by a growth phase.

EXAMPLE 3

The following examples illustrate the carrying out of the process of the present invention with variable pH in the pre-treatment period. The conditions used are described in the following protocol and the results are given in Table III.

PROTOCOL:

| | |
|---|---|
| Molasses | 758g at 85° Brix, fed incrementally over 16¼ hr. period. |
| Seed Yeast | Bakers' yeast (*Saccharomyces cerevisiae*) was used in the amounts as indicated. |
| Starting Volume | 3400 ml. |
| Final Volume | About 5000 ml. |
| Salts | 1.7g each of KCl and $MgSO_4 \cdot 7H_2O$; 16.8g $(NH_4)H_2PO_4$ |
| $CrCl_3 \cdot 6H_2O$ | 0.5g, added to starting volume with seed yeast 30 minutes prior to starting feed. |
| Pre-treatment pH | 5.2 or 4.0 |
| Growth Phase pH | 5.25 |
| Temperature | 29° ± 1° C. |
| Growth Time | 17 hours |
| Washing Cycles | 4 |
| Typical Final Yeast Products Analysis | Moisture 3–6% |
| | Protein 40–58% (% N × 6.25) |
| | Phosphate 1.7–3.5% (as $P_2O_5$) |
| | Chromium 40–200 μg/g yeast solids |

TABLE III

| Run | Amount of Seed Yeast (g solids) | Pre-treatment pH | Amount of Final Yeast (g solids) | Intracellular $Cr^{+3}$ in Yeast Product (μg/g Yeast Solids) | Percent Uptake |
|---|---|---|---|---|---|
| A | 30 | 5.25 ± .15 | 217 | 88.4 | 19.7 |
| B | 30 | 4.0 ± .2 | 228 | 16.0 | 3.7 |
| C | 30 | 5.25 ± .15 | 210 | 94.4 | 20.3 |

Runs A and C show the reproducibility of the results. The fermentation growth in all cases was about a six-fold increase. It can be clearly seen that the pH of the pre-treatment is a determinant of the amount of chromium in the final yeast product (cf. run B with runs A and C).

Additional experiments indicated that the addition of chromium salts to the seed yeast just prior to starting the feed of nutrients resulted in very low levels of chromium in the final yeast product.

EXAMPLE 4

The following examples illustrate the carrying out of the process of the present invention with various concentrations of seed yeast as shown in Table IV. Other conditions were as described in Example 3.

TABLE IV

| Amount of Seed Yeast (g solids) | Amount of Final Yeast (g solids) | Intracellular $Cr^{+3}$ in Yeast Product (μg/g Yeast Solids) | Percent Uptake | Calculated $Cr^{+3}$ in Seed Yeast (μg/g) Yeast Solids |
|---|---|---|---|---|
| 25 | 40 | 939 | 38.3 | 1496 |
| 30 | 157 | 187 | 30.1 | 1010 |
| 35 | 216 | 141 | 31.1 | 869 |

The results show that more than about 1000 μg of chromium per gram of yeast solids absorbed by the seed yeast will lead to reduced growth of the yeast.

These experiments illustrate within normal experimental variability that the intracellular absorption of chromium by the seed yeast at levels of less than 1000 μg/g of yeast solids does not interfere with normal growth of the yeast under typical fermentation conditions (i.e., about a seven-fold increase in yeast solids in a 17-hour period). However, at increasing levels of chromium ion absorption by the seed yeast (at levels at or above about 1000 μg/g of yeast solids) substantial deviations from normally expected growth are observed including essentially complete inhibition of yeast growth at higher chromium ion levels.

EXAMPLE 5

An experiment was run to demonstrate the effect of length of fermentation time on yeast growth and consequent chromium content of the yeast products produced. The protocol used was as follows:

| PROTOCOL: | |
|---|---|
| Pre-treatment: | Starting volume - 360 gallons |
| | Seed yeast - 34.2 lb. solids |
| | $CrCl_3.6H_2O$ - 270 g |
| | 30 minutes agitation at pH 5.25 |
| Fermentation: | Salts added - 1.4 lb. each KCl and $MgSO_4.7H_2O$ |
| | Molasses - 620 lb at 85° Brix, fed incrementally over a period of 12 hrs |
| | Phosphoric acid 7.2 lbs. - fed incrementally in the first 3 hrs. |
| | Ammonium hydroxide - 53.6 lbs. delivered incrementally in the first 9.5 hrs. |
| | Sulfuric acid - as needed for pH control |

The results are shown in Table V following:

TABLE V

| Length of Fermentation (hrs) | Total Yeast Solids (lbs) | Intracellular $Cr^{+3}$ in Yeast Product (μg/g yeast solids) | Percent Uptake |
|---|---|---|---|
| 0 | 34.2 | * | *— |
| 3 | 57.8 | 265 | 13.2 |
| 6 | 91.1 | 212 | 16.6 |
| 9 | 123.7 | 135 | 14.4 |
| 12.5 | 152.8 | 89 | 11.7 |

*not determined

These results demonstrate that the intracellular chromium ion in the yeast is diluted by yeast growth and that there is little if any chromium taken up by the yeast from the media during the fermentation or growth period.

EXAMPLE 6

The following illustrates the process of the present invention on a larger scale.

A large-scale trial was conducted. The results shown in Table VI were comparable to those obtained in Example 5.

| PROTOCOL | |
|---|---|
| Pre-treatment: | Starting volume - 29,000 gallons |
| | Seed yeast - 3,000 lb solids |
| | $CrCl_3.6H_2O$ - 46 lb |
| | 30 minutes at pH 5.25 |
| Fermentation: | Salts added - 100 lb each KCl and $MgSO_4.7H_2O$ |
| | Molasses - 44,600 lb at 85° Brix fed incrementally over a period of 12 hrs |
| | Phosphoric acid - 660 lb over a period of the first 3 hrs. |
| | Ammonium hydroxide - 4,500 lb delivered in parallel feed with the molasses |
| | Sulfuric acid - as needed to control pH |

TABLE VI

| Time (hrs) | Yeast Solids (lbs) | Intracellular $Cr^{+3}$ in Yeast Product (μg/g of yeast solids) | Percent Uptake |
|---|---|---|---|
| 0 | 2,738 | 402 | 10.7 |
| 3 | 4,024 | 224 | 10.9 |
| 6 | 6,900 | 154 | 12.2 |
| 9 | 9,960 | 104 | 11.1 |
| 12.5 | 13,631 | 64 | 9.6 |

What is claimed is:

1. A process for producing a chromium yeast product which comprises:
   (a) adjusting the pH of an aqueous suspension of live edible, food grade yeast cells from about 4 to about 7;
   (b) treating an aqueous suspension of live yeast cells with a water-soluble, non-toxic chromium salt at a chromium ion concentration based on yeast cell solids that is below the concentration at which an inhibitory effect on the growth of the yeast is observed;
   (c) maintaining the suspension for an essentially non-growth pre-treatment period sufficient to permit substantial intracellular absorption of chromium by said yeast cells;
   (d) adding yeast growth nutrients to the aqueous medium containing the chromium-treated yeast and induce growth of the said yeast to thereby dilute the intracellular chromium content of said yeast to a predetermined level;
   (e) recovering and concentrating the yeast cells from the aqueous growth medium;
   (f) washing the recovered yeast cells to remove extracellular chromium salts; and
   (g) pasteurizing and drying the washed yeast cells containing a substantial amount of intracellular chromium ion.

2. A process according to claim 1 wherein the pre-treatment period is at least about 5 minutes.

3. A process according to claim 2 wherein the pre-treatment period is at least between about 5 to about 30 minutes.

4. A process according to claim 1 wherein the pH of said medium during the non-growth, pre-treatment period is maintained at between about 5 and 6.

5. A process according to claim 1 wherein chromium ion concentration in the medium during said pre-treatment period is between about 500 and 6000 μg/g based on yeast solids.

6. A process according to claim 1 wherein the pH of the medium containing the chromium treated yeast is adjusted to between about 4.5 and 5.5 during said growth period.

7. A process according to claim 1 wherein said growth period is sufficient to at least double the number of yeast cells.

8. A process according to claim 1 wherein the intracellular chromium ion content of the recovered yeast cells is at least 40 ppm.

9. A process according to claim 1 wherein the growth period is maintained for a period from about 4 to about 17 hours.

10. A process according to claim 1 wherein the yeast is *Saccharomyces cerevisiae*.

11. A process according to claim 1 wherein the yeast is Brewer's yeast.

12. A method of preparing a chromium yeast product which has a high intracellular chromium content which comprises:
   (a) adjusting the pH of an aqueous suspension of live edible food grade yeast cells to from about 4 to about 7;
   (b) treating the aqueous suspension of live yeast cells with a water-soluble, non-toxic chromium salt at a chromium ion concentration, of from about 200 to 8000 μg/g of yeast cell solids;
   (c) maintaining said yeast cells in contact with chromium ion at said pH levels in the medium under essentially non-growth conditions for a period of at least about 5 to 30 minutes until said yeast cells have intracellularly absorbed a substantial amount of chromium ion;
   (d) recovering and concentrating the yeast cells from the aqueous medium;
   (e) washing the recovered yeast cells to remove extracellular chromium salts; and
   (f) pasteurizing, and drying the washed yeast cells containing a substantial amount of intracellular chromium ion.

13. A method according to claim 12 wherein the chromium ion concentration is from 1000 to 4000 μg/g of yeast solids.

14. A method according to claim 12 wherein the pH is from about 5 to about 6.

* * * * *